(12) United States Patent
Jang

(10) Patent No.: US 11,517,508 B2
(45) Date of Patent: Dec. 6, 2022

(54) COMPOSITION FOR SINGLE-PASTE TYPE HYDRAULIC ENDODONTIC FILLING MATERIAL COMPRISING DIMETHYL SULFOXIDE

(71) Applicant: MARUCHI, Wonju-si (KR)

(72) Inventor: Sung Wook Jang, Seoul (KR)

(73) Assignee: MARUCHI

( * ) Notice: Subject to any disclaimer, the term of this patent is extended or adjusted under 35 U.S.C. 154(b) by 817 days.

(21) Appl. No.: 16/462,927

(22) PCT Filed: Nov. 21, 2017

(86) PCT No.: PCT/KR2017/013300
§ 371 (c)(1),
(2) Date: May 21, 2019

(87) PCT Pub. No.: WO2018/093241
PCT Pub. Date: May 24, 2018

(65) Prior Publication Data
US 2019/0321267 A1    Oct. 24, 2019

(30) Foreign Application Priority Data

Nov. 21, 2016 (KR) ........................ 10-2016-0155276

(51) Int. Cl.
| | |
|---|---|
| *A61K 6/853* | (2020.01) |
| *A61K 6/54* | (2020.01) |
| *A61K 6/76* | (2020.01) |
| *A61K 6/869* | (2020.01) |
| *A61K 6/73* | (2020.01) |
| *A61K 6/69* | (2020.01) |

(Continued)

(52) U.S. Cl.
CPC ................ *A61K 6/853* (2020.01); *A61K 6/54* (2020.01); *A61K 6/56* (2020.01); *A61K 6/69* (2020.01); *A61K 6/73* (2020.01); *A61K 6/76* (2020.01); *A61K 6/80* (2020.01); *A61K 6/869* (2020.01)

(58) Field of Classification Search
CPC ...................................... A61K 6/853
See application file for complete search history.

(56) References Cited

U.S. PATENT DOCUMENTS

| 5,573,583 A | 11/1996 | Kondo |
| 2007/0009858 A1 | 1/2007 | Hatton et al. |

(Continued)

FOREIGN PATENT DOCUMENTS

| CN | 106163488 A | 11/2016 |
| KR | 20100037979 A | 4/2010 |

(Continued)

OTHER PUBLICATIONS

European Patent Office, Patent Search Report dated Jun. 8, 2020.
WIPO, International Search Report dated Feb. 19, 2018.
China Patent Office, Office action dated Sep. 28, 2021.

*Primary Examiner* — Benjamin J Packard
(74) *Attorney, Agent, or Firm* — Dinsmore & Shohl LLP

(57) ABSTRACT

The present invention relates to a composition for a single-paste type hydraulic endodontic filling material comprising dimethyl sulfoxide (DMSO). According to one aspect of the invention, there is provided a single-paste type hydraulic endodontic filling composition, comprising a calcium silicate component and DMSO.

6 Claims, 4 Drawing Sheets

(51) Int. Cl.
*A61K 6/56* (2020.01)
*A61K 6/80* (2020.01)

(56) References Cited

U.S. PATENT DOCUMENTS

| | | | |
|---|---|---|---|
| 2010/0248190 A1* | 9/2010 | Chen | A61K 6/90 433/215 |
| 2013/0023601 A1 | 1/2013 | Ogliaari et al. | |
| 2014/0050674 A1 | 2/2014 | Tjaderhane | |

FOREIGN PATENT DOCUMENTS

| | | |
|---|---|---|
| KR | 10-2015-0100446 A | 9/2015 |
| WO | WO 2008/100452 A2 | 8/2008 |
| WO | WO 2012/146832 A2 | 11/2012 |

\* cited by examiner

COMPOSITION FOR SINGLE-PASTE TYPE HYDRAULIC ENDODONTIC FILLING MATERIAL COMPRISING DIMETHYL SULFOXIDE

CROSS-REFERENCE TO RELATED APPLICATION(S)

This application is a continuation application of Patent Cooperation Treaty (PCT) international application Serial No. PCT/KR2017/013300, filed on Nov. 21, 2017, which claims priority to Korean Patent Application Serial No. 10-2016-0155276, filed on Nov. 21, 2016. The entire contents of PCT international application Serial No. PCT/KR2017/013300 and Korean Patent Application Serial No. 10-2016-0155276 are hereby incorporated by reference.

FIELD OF THE INVENTION

The present invention relates to a composition for a single-paste type hydraulic endodontic filling material comprising dimethyl sulfoxide (DMSO).

BACKGROUND

Generally, a medical cement composition is used in various fields as a material to be filled in a space from which nerves, blood vessels, cellular tissues and the like have been removed. Particularly, in the field of dentistry, the use of the medical cement composition is essential when endodontic treatment is performed by removing nerves, blood vessels and other cellular tissues inside a tooth and then filling and sealing the space with the material to maintain the function of the tooth.

Mineral trioxide aggregate (MTA) is a medical cement composition widely used for root canal treatment. It is mainly used for restoration of root perforation sites, pulpotomy, partial pulpotomy, pulp capping, root canal filling, root-end retrofilling, and the like. MTA has good sealing properties and biocompatibility and is superior to calcium hydroxide, which is mainly used for pulp treatment of vital teeth, in terms of tertiary dentin formation or inflammatory cell infiltration.

MTA comprises calcium silicate, calcium aluminate and gypsum as main components. Calcium silicate reacts with water to produce calcium silicate hydrate (C—S—H) and calcium hydroxide in an environment where body fluids, saliva and other liquids are present. Here, it is generally assumed that 75% of the product produced by the hydration reaction of MTA is calcium silicate hydrate (C—S—H) and the remaining 25% is calcium hydroxide. Calcium aluminate is added to control hardening time because the hydration reaction of calcium silicate requires a considerably long time. Calcium aluminate forms ettringite at the early stage of the hydration to generate initial strength. At this time, manipulability may be deteriorated when the hydration reaction is excessively rapid. Thus, gypsum is additionally mixed at about 40 to 100 wt % with respect to calcium aluminate. As the gypsum, anhydrous or hemihydrate gypsum is used rather than dihydrate gypsum. Among the hemihydrate gypsum, alpha-hemihydrate is preferred over beta-hemihydrate in terms of volume stability. Among various types of the anhydrous gypsum, type II is particularly preferred.

Since MTA adheres to surrounding hard tissues as it hardens by reacting with water, it has better sealing properties than conventionally used amalgam, IRM, Super EBA and the like, while it has disadvantages such as long hardening time, poor manipulability and discoloration. Further, since MTA is greatly influenced by its surroundings during the hydration process, there is a problem that MTA is washed away without being hardened when inflammation is present or bleeding is severe. The poor manipulability is the greatest barrier for users (or dentists) who use MTA, and a lot of time, effort, and trial and error are required particularly when powdered MTA is mixed with a liquid and applied into a narrow and deep root canal.

Recently, MTA sealer has been popularized which is provided in the form of a single paste and comprises a mixture of NMP (N-methyl-2-pyrrolidone) and calcium silicate cement. Its usability, good sealing properties, and treatment safety have been verified by a lot of experiments, and it has consequently received considerable attention. Here, NMP may be provided as kneaded with calcium silicate and hardened in a human body. Although NMP is a liquid that has been medically recognized to be safe for human use through long verification periods, it is not particularly suitable for a regenerative endodontic procedure that requires safety to such a degree that there is no toxicity to the human body and stem cell differentiation is not influenced.

Diethyl sulfoxide (DMSO) is a polar solvent like NMP and has a viscosity similar to that of water so that it is easily substituted. DMSO has been used for a long time in human bodies and proved to be safe and effective. Dietary sulfur is referred to as MSN (DMSO2) when it exists in a solid state at room temperature, and referred to as DMSO when it exists in a liquid state. DMSO is mainly used for rheumatoid arthritis, ankylosing spondylitis, eczema, acne, pustular skin disease, periodontitis, pulpitis, and the like due to its anti-inflammatory pharmacological action. It is frequently used as a drug carrier in functional cosmetics due to its properties of enhancing permeability of other materials. Further, DMSO is known to have the abilities to induce the differentiation of cells degenerated into cancer cells or the like, and to inhibit the growth of the cells. Thus, histone deacetylase inhibitors have been developed from various derivatives such as HMBA, SBHA, SAHA, and TSA, which utilize the structural formula of DMSO. These derivatives are used as anticancer drugs for treating various types of cancers. In addition, DMSO has good solubility and permeability into cell tissues, and has the excellent ability to preserve cells from frost damage. Due to these properties, DMSO is widely used not only for cell cryopreservation but also for human cryopreservation, which is a means to treat currently incurable diseases in the future.

SUMMARY OF THE INVENTION

One object of the present invention is to solve all the above-described problems in the prior art.

Another object of the invention is to provide an endodontic filling material that has good biocompatibility and does not cause a toxic reaction in a human body to ensure more safety.

Yet another object of the invention is to provide a single-paste type hydraulic endodontic filling material that is provided in a kneaded state and hardens by absorbing surrounding water to seal a perforation site of a root canal or tooth three-dimensionally.

The representative configurations of the invention to achieve the above objects are described below.

According to one aspect of the invention, there is provided a single-paste type hydraulic endodontic filling composition, comprising a calcium silicate component and DMSO.

In addition, there are further provided other endodontic filling compositions to implement the invention.

According to the invention, there is provided an endodontic filling material that has good biocompatibility and does not cause a toxic reaction in a human body to ensure more safety.

According to the invention, there is provided a single-paste type hydraulic endodontic filling material that is provided in a kneaded state and hardens by absorbing surrounding water to seal a perforation site of a root canal or tooth three-dimensionally.

DETAILED DESCRIPTION

Figure 1:
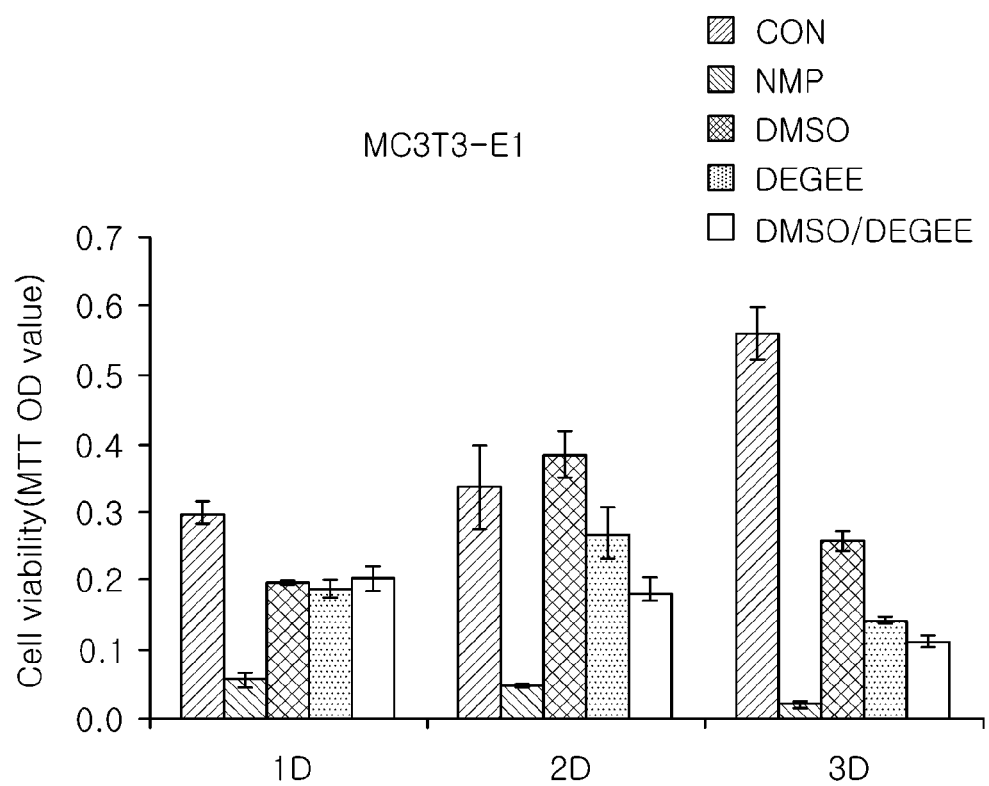
FIG. 1 is a graph of a cytotoxicity test according to one embodiment of the invention.

In the following detailed description of the present invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures, components, and characteristics described herein may be implemented as modified from one embodiment to another without departing from the spirit and scope of the invention. Furthermore, it shall be understood that the locations or arrangements of individual elements within each of the embodiments, or the conditions or orders of the mixtures, reactions and the like of the individual elements, may also be modified without departing from the spirit and scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, various preferred embodiments of the present invention will be described in detail with reference to the accompanying drawings to enable those skilled in the art to easily implement the invention.

PREFERRED EMBODIMENTS OF THE INVENTION

The composition of a single-paste type hydraulic endodontic filling material according to one embodiment of the invention may be largely divided into powder components and liquid components, as will be described below.

(1) Powder Components

The powder components may comprise a calcium silicate component that causes a hydration reaction. The types of the calcium silicate component may include calcium trisilicate and calcium disilicate. In particular, calcium trisilicate may be freely selected from three types of triclinic system T1, T2 and T3, three types of monoclinic system M1, M2 and M3, and a rhombohedral system. Preferably, an M3 or R-phase that has a non-centrosymmetric structure may be selected. Preferably, calcium disilicate may also be β-C2S that has a non-centrosymmetric structure. The main reason why the calcium silicate compound having a non-centrosymmetric structure is selected is because it has good reactivity with water and the unreacted calcium silicate compound remaining after hydration has good biosafety.

Although calcium hydroxide produced by the hydration of the above calcium silicate component is effective and safe in root canals in the early stage, it may weaken dentine by reacting with collagen that forms the dentine when it remains therein for an excessively long period of time. Thus, it may be preferred to additionally include a pozzolanic material that consumes the calcium hydroxide. Amorphous silica such as fumed silica, precipitated silica and colloidal silica may be selected as the pozzolanic material. Besides, metakaolin, diatomite, swelling clay (e.g., swelling phyllosilicates) and the like may be suitably used. In particular, swelling phyllosilicates have the advantages of providing an appropriate viscosity for injecting a paste, and providing a rate of expansion suitable for an endodontic filling material during a hardening process. Suitable examples of swelling phyllosilicates may include bentonite, hectorite and synthetic swelling clay, and bentonite may be most preferred since it has good antibacterial properties. Bentonite has the advantage of acquiring pozzolanic reactivity when it is heat-treated at 700° C. or higher, and it is known that the antibacterial properties are maintained even thereafter. However, since the heat treatment removes the swelling properties, bentonite without pozzolanic reactivity may be suitable for appropriate expansion.

Further, a radiopaque material may be further included as a powder component. It may be preferred to add the radiopaque material in an amount slightly more than the international standard ISO 13485 for better radiopacity, because the radiopaque material assists a user to check whether a filling material injected by the user is sufficiently transferred to a desired location. For example, powders such as bismuth titanate, barium titanate, barium zirconate, zirconium oxide, tantalum oxide, and calcium tungstate may be preferred which are safe, non-toxic and less leaching in a human body. It may be preferred to exclude a component such as bismuth oxide since it can discolor dentine and leach well. Among these, barium titanate or zirconium oxide powder may be most preferred.

In addition, a suitable viscosity enhancing agent may be added. Preferred components for the viscosity enhancing agent may include at least one selected from cellulose derivatives (e.g., methyl cellulose, hydroxypropyl methylcellulose and carboxymethyl cellulose), chitin, chitosan derivatives, bentonite, hectorite, and sugar alcohols. The viscosity enhancing agent may be any component capable of imparting viscosity while dissolving or dispersing in DMSO, as long as it is suitable for use in a human body without interfering with hardening.

(2) Liquid Components

The liquid components may comprise DMSO. DMSO exists as a solid at room temperature, which may be inconvenient for normal use. Thus, it may be preferred to lower the freezing point thereof by further adding one or a combination of two or more of water, ethanol, monoethylene glycol, and diethylene glycol monoethyl ether (DEGEE) in a minimal amount. However, in any case, it may be preferred that the weight ratio of the added liquid is 30% or less of the weight of the total liquid components. That is, it may be preferred that the weight ratio of DMSO is at least 70% of the weight of the liquid components. A lower content thereof may affect transdermal absorption and reduce anti-inflammatory and analgesic effects.

In the following, tests and evaluations performed with respect to various embodiments of the invention will be described.

(1) Cytotoxicity Evaluation

FIG. 1 is a graph of a cytotoxicity test according to one embodiment of the invention. The test will be described with reference to FIG. 1.

A: NMP, B: DMSO, C: DEGEE, and D: DMSO 80%+ DEGEE 20%

Cytotoxicity was measured with respect to the above four kinds of solvents by the following method:

(i) A specimen was placed in a mold with a thickness of 2 mm and a diameter of 10 mm, and hardened in an incubator at 37° C. for 3 days. (ii) A material extract was derived by filling the hardened specimen with a medium at a surface area/medium ratio of 0.5 $cm^2$ per ml and incubating it at 37° C. for 3 days. (iii) $1.5 \times 10^4$ MC3T3-E1 cells were seeded per well on a 24-well culture plate and incubated for 24 hours, and then the medium was sucked off. 1 ml of the material extract was placed in each well and set in triplicate. (iv) The material extracts were incubated for 24 hours, 48 hours and 72 hours, respectively, and then the medium was discarded. The material extracts were treated with 200 μl of 0.05% MTT solution, wrapped in aluminum foil, and reacted in the incubator at 37° C. for 2 hours. (v) 200 μl of DMSO was added after the reaction. Then, 200 μl of the reaction solution was transferred to each well on a 96-well plate and absorbance was measured at 590 nm.

The results of the above test are shown in FIG. 1 and described as below. (i) In all tests and at all times, groups for which DMSO, DEGEE, and a mixture of DMSO and DEGEE were used as solvents showed a higher cell survival rate than groups for which NMP was used as a solvent, with statistical significance ($p<0.05$). (ii) For the cases of 48 hours and 72 hours, groups for which DMSO was used as a solvent showed a significantly higher cell survival rate than groups for which DEGEE and a mixture of DMSO and DEGEE were used as solvents ($p<0.05$). (iii) For the cases of 48 hours and 72 hours, groups for which a mixture of DMSO and DEGEE was used as a solvent showed a significantly lower cell survival rate than other groups ($p<0.05$).

(2) A Paste According to One Embodiment of the Invention

Preparation Example

According to one embodiment of the invention, zirconium oxide, calcium trisilicate, bentonite, fumed silica, and hydroxypropyl methylcellulose were mixed with DMSO to prepare a paste. The above components were mixed at a weight ratio of 45:21:1:0.6:0.6:31.8 (in the above order).

Cytotoxicity

Figure 2:
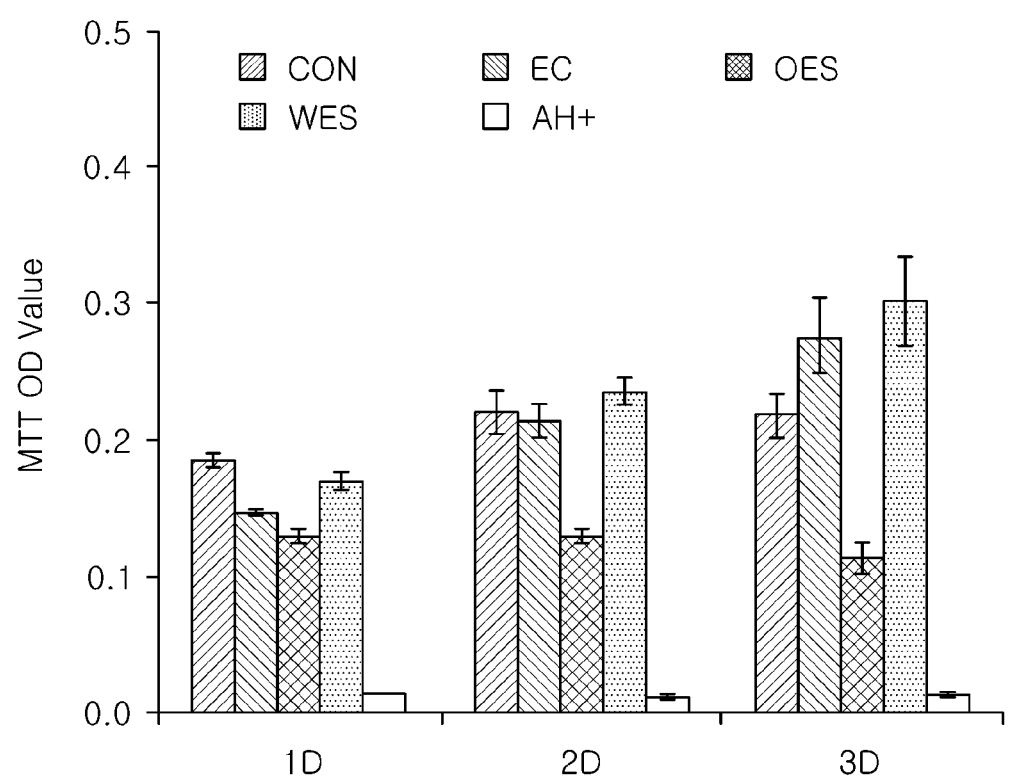
FIG. 2 is a graph of a cytotoxicity test according to one embodiment of the invention.

FIG. 2 is a graph of a cytotoxicity test according to one embodiment of the invention. The test will be described with reference to FIG. 2.

EC: a conventional endocem MTA product mixed with water,

OES: a conventional endoseal MTA product which is a single-paste type hydraulic endodontic filling material using NMP as a solvent, WES: a paste prepared according to the embodiment using DMSO as a solvent, and AH+: an AH plus product which is a commercially available resin type (not MTA) sealer Cytotoxicity was measured with respect to the above four kinds of products/compositions by the following method:

(i) A specimen was placed in a mold with a thickness of 2 mm and a diameter of 10 mm, and hardened in an incubator at 37° C. for 3 days. (ii) A material extract was derived by filling the hardened specimen with a medium at a surface area/medium ratio of 0.5 $cm^2$ per ml and incubating it at 37° C. for 3 days. (iii) $1.5 \times 10^4$ MC3T3-E1 cells were seeded per well on a 24-well culture plate and incubated for 24 hours, and then the medium was sucked off. 1 ml of the material extract was placed in each well and set in triplicate. (iv) The material extracts were incubated for 24 hours, 48 hours and 72 hours, respectively, and then the medium was discarded. The material extracts were treated with 200 μl of 0.05% MTT solution, wrapped in aluminum foil, and reacted in the incubator at 37° C. for 2 hours. (v) 200 μl of DMSO was added after the reaction. Then, 200 μl of the reaction solution was transferred to each well on a 96-well plate and absorbance was measured at 590 nm.

Figure 3:
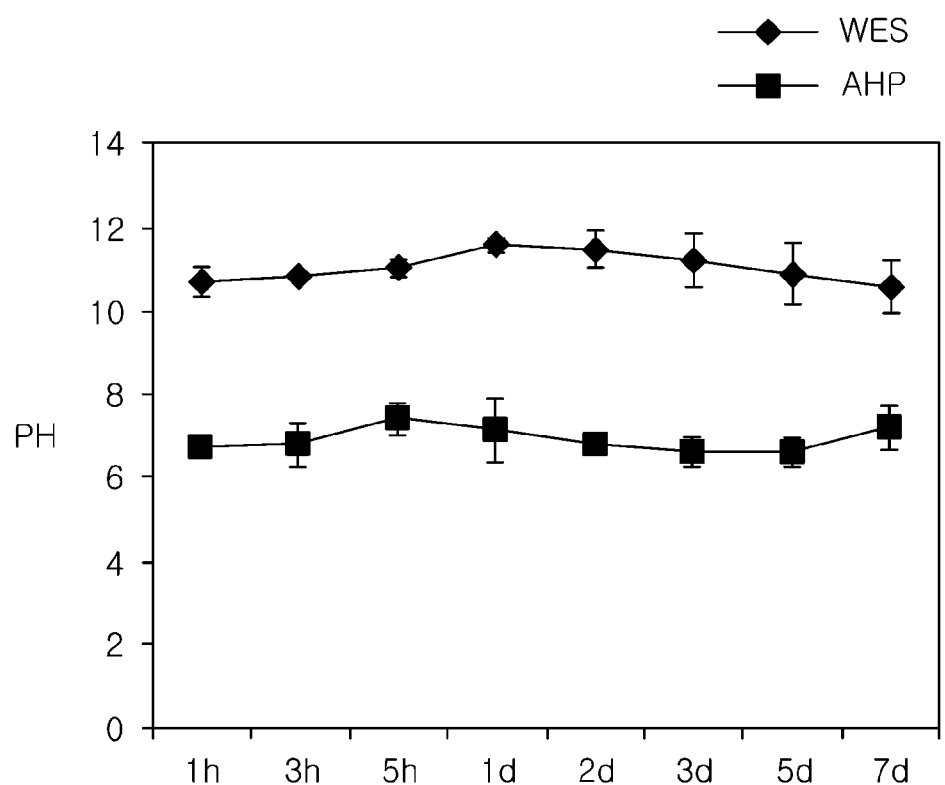
FIG. 3 is a graph of a pH change test according to one embodiment of the invention.

As shown in FIG. 3, WES showed a cell survival rate similar to that of the control group on day 1 and day 2, and showed a cell survival rate higher than that of the control group on day 3 ($p<0.05$). Further, the cell survival rate of WES was higher than that of OES ($p>0.05$) and similar to that of EC ($p<0.05$). It seems that WES has lower cytotoxicity than OES because OES uses NMP as a solvent while WES uses DMSO. Consequently, FIG. 2 demonstrates that WES exhibits better biocompatibility than conventional products.

pH Change

A pH change of the paste prepared according to the embodiment was observed. WES was used as an experimental group and AH plus, which is a resin type material, was used as a control group. Each material was injected into a mold having a thickness of 1 mm and a diameter of 5 mm and then hardened. Thereafter, the hardened materials were put in 10 ml of distilled water and pHs were measured from 1 hour to 7 days using a pH meter. FIG. 3 is a graph of a pH change test according to one embodiment of the invention, and shows the results of the above test. WES maintained a pH of 10 or higher throughout the test period, while AH plus showed a pH corresponding to neutrality. It seems that this is because fumed silica consumes calcium hydroxide, which is a strong base.

Solubility

It is preferred that an endodontic filling material is not dissolved in a root canal by a tissue fluid or the like as much as possible. It is because bacteria may multiply in the dissolved space and reinfection may occur if the solubility of the material is high. That is, the hermeticity is better as the solubility is lower.

The paste prepared according to the embodiment was injected into a mold having a thickness of 1.5 mm and a diameter of 20 mm and then hardened. The weight of each specimen was measured and set as W1. Each specimen was immersed in 10 ml of distilled water and then taken out on the seventh day. The weight of each specimen was measured again and set as W2. The solubility was calculated using a formula of Solubility (s)=(W1−W2)/W1×100. The result showed a fairly good solubility of 1.19±0.11%.

Volume Change

Once an endodontic filling material is applied within a root canal, its original volume should be kept almost intact and it should not shrink as much as possible. If the material shrinks, it will inevitably leave an empty space and conditions for bacterial multiplication may be created. A single-paste type MTA sealer should have a small volume change, which is the most important property of the sealer, and should have a swelling capacity of about 2%.

The paste prepared according to the embodiment was injected into a silicone mold having a diameter of 6 mm and a length of 12 mm and then hardened. Thereafter, the material was removed from the mold and then its length was measured and set as M1. Next, the material was kept in distilled water at 37° C. and taken out after 7 days. The length was measured again and set as M2. A volume change D was calculated by D=(M2−M1)/M2×100. The result showed a good volume change of 2.25±0.28%, which is less than 5%.

Antibacterial Activity

Figure 4:
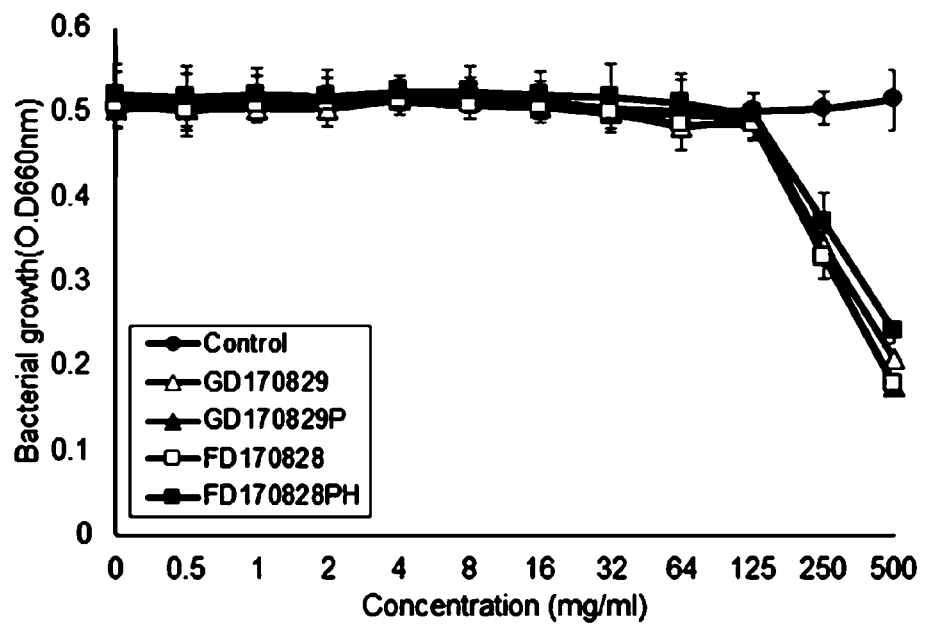
FIG. 4 is a graph showing a situation in which a specimen according to a preparation example of the invention and a specimen of bentonite heat-treated at 900° C. in the preparation example are applied to *E. faecalis* having a biofilm, respectively.
Figure 5:
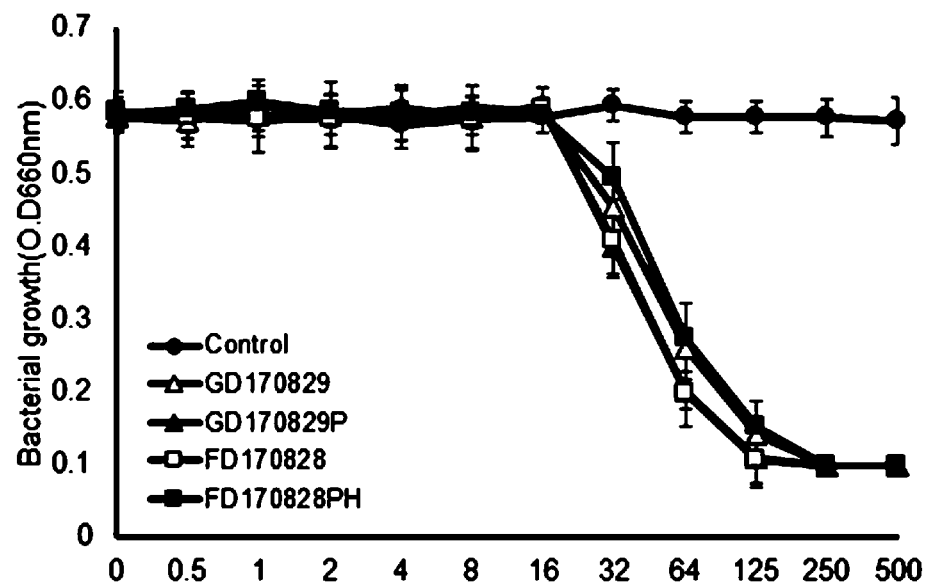
FIG. 5 is a graph showing a situation in which the above specimens are applied to *P. endodontalis* having a biofilm, respectively.

FIG. 4 is a graph showing a situation in which a specimen according to the preparation example (FD170828) and a specimen of bentonite heat-treated at 900° C. (the heat treatment is intended to maintain antibacterial activity while controlling expansion) in the preparation example (FD170828PH) are applied to *E. faecalis* having a biofilm, respectively. FIG. 5 is a graph showing a situation in which the above specimens are applied to *P. endodontalis* having a biofilm, respectively. The description of the other two specimens will be omitted for convenience.

For the tests of FIGS. 4 and 5, as bacteria, *E. faecalis* ATCC 29221 was cultured at 37° C. in an aerobic condition using a brain heart infusion (BHI) medium (BD bioscience, Sparks, Md., USA) and *P. endodontalis* ATCC 35406 was cultured at 37° C. in an anaerobic condition (5% of $H_2$, 10% of $CO_2$ and 85% of $N_2$) using a brain heart infusion liquid medium containing 1 μg/ml of hemin and 0.2 μg/ml of vitamin K.

First, *E. faecalis* was inoculated on a 12-well plate and cultured for one week in an anaerobic state, while the existing liquid medium was removed and replaced with a fresh liquid medium by 1 ml on every day. The medium was removed after one week and then 0.5 mg of FD170828 and FD170828PH were applied and allowed to stand at 37° C. in an anaerobic state for 2 hours. Then, 1 ml of a BHI liquid medium was added and the biofilm was removed with a scrapper. 2 ml of suspension was transferred to a tube and centrifuged at 1,000×g for 10 minutes to remove sample particles. Supernatant containing the bacteria was transferred to a clean tube. Thereafter, the suspension containing the bacteria was diluted 10-fold and inoculated in a BHI solid medium, and then the number of the bacteria was measured. In order to measure the number of the bacteria, a method of measuring absorbance at a wavelength of 660 nm using a micro-reader was used.

In addition, the above process was performed for *P. endodontalis* in a similar manner.

As a result, it can be seen that antibacterial activity was excellent in both cases of FIGS. 4 and 5, as shown.

What is claimed is:

1. A single-paste type hydraulic endodontic filling composition, comprising:
   a calcium silicate component; and
   dimethyl sulfoxide (DMSO),
   wherein the DMSO is included at 70% or more of weight of liquid components of the single-paste type hydraulic endodontic filling composition, and
   wherein at least one selected from a group consisting of water, ethanol, polyethylene glycol, and diethylene glycol monoethyl ether (DEGEE) is included at 30% or less of the weight of the liquid components.

2. The single-paste type hydraulic endodontic filling composition of claim 1, further comprising a pozzolanic material.

3. The single-paste type hydraulic endodontic filling composition of claim 2, wherein the pozzolanic material is at least one of fumed silica, precipitated silica and colloidal silica.

4. The single-paste type hydraulic endodontic filling composition of claim 1, further comprising at least one of metakaolin, diatomite and swelling clay.

5. The single-paste type hydraulic endodontic filling composition of claim 4, wherein the swelling clay comprises at least one of bentonite, hectorite and synthetic swelling clay.

6. The single-paste type hydraulic endodontic filling composition of claim 1, further comprising a radiopaque material, and
   wherein the radiopaque material is selected from barium titanate, bismuth titanate, barium zirconate, zirconium oxide, calcium tungstate, tantalum oxide, and mixtures of two or more of the foregoing.

* * * * *